(12) United States Patent
Kohno et al.

(10) Patent No.: US 6,527,917 B1
(45) Date of Patent: Mar. 4, 2003

(54) PROCESS FOR PREPARING PENTAFLUOROETHANE

(75) Inventors: Satoru Kohno, Settsu (JP); Takashi Shibanuma, Settsu (JP)

(73) Assignee: Daikin Industries Ltd., Osaka (JP)

( * ) Notice: Subject to any disclaimer, the term of this patent is extended or adjusted under 35 U.S.C. 154(b) by 0 days.

(21) Appl. No.: 09/485,869

(22) PCT Filed: Aug. 12, 1998

(86) PCT No.: PCT/JP98/03590

§ 371 (c)(1),
(2), (4) Date: Mar. 20, 2000

(87) PCT Pub. No.: WO99/10302

PCT Pub. Date: Mar. 4, 1999

(30) Foreign Application Priority Data

Aug. 21, 1997 (JP) .............................. 9-224989

(51) Int. Cl.$^7$ .......................... B01D 3/40; C07C 17/380
(52) U.S. Cl. ............................ 203/67; 203/78; 570/178
(58) Field of Search .................. 203/57, 67, 71, 203/78, 100; 570/178, 177, 180

(56) References Cited

U.S. PATENT DOCUMENTS

| | | | | |
|---|---|---|---|---|
| 5,087,329 A | | 2/1992 | Felix | 570/128 |
| 5,211,867 A | * | 5/1993 | Shankland et al. | 203/67 |
| 5,421,964 A | * | 6/1995 | Mahler et al. | 203/51 |
| 6,039,845 A | * | 3/2000 | Bartocchio et al. | 203/57 |
| 6,156,161 A | * | 12/2000 | Miller | 203/67 |

FOREIGN PATENT DOCUMENTS

| | | |
|---|---|---|
| JP | 8143486 | 6/1996 |
| JP | 8143486 A | 6/1996 |
| JP | 9255597 | 9/1997 |
| JP | 9508626 | 9/1997 |
| JP | 9508626 A | 9/1997 |
| JP | 9512793 | 12/1997 |
| JP | 9512793 A | 12/1997 |
| WO | WO9220640 A1 | 11/1992 |
| WO | WO9521147 A1 | 8/1995 |
| WO | WO9527689 A1 | 10/1995 |
| WO | WO9606063 | 2/1996 |

OTHER PUBLICATIONS

Schweitzer, "Handbook of Separation Techniques for Chemical Engineers", PP1–136 –1–138.*

* cited by examiner

Primary Examiner—Virginia Manoharan
(74) Attorney, Agent, or Firm—Birch, Stewart, Kolasch & Birch LLP

(57) ABSTRACT

A method for efficiently separating pentafluoroethane (HFC-125) from a mixture thereof with chloropentafluoroethane (CFC-115). This method is performed by subjecting a mixture (2) of HFC-125 (6) and CFC-115 (4) to extractive distillation (1) to give highly concentrated HFC-125 (6). A hydrofluorocarbon compound (3) having two carbon atoms, particularly 1,1,1,2-tetrafluoroethane, is used as an extractant to obtain concentrated CFC-115 as a distillate and a mixture of HFC-125 having a reduced content of CFC-115 with the extractant as a bottom (5), the extractant being separated from HFC-124 in this mixture by distillation (9) and reused in the extractive distillation.

4 Claims, 1 Drawing Sheet

US 6,527,917 B1

PROCESS FOR PREPARING PENTAFLUOROETHANE

This application is the national phase under 35U.S.C. §371 of PCT International Application No. PCT/JP98/03590 which has an International filing date of Aug. 12, 1998, which designated the United States of America.

TECHNICAL FIELD

The present invention relates to a process of separating pentafluoroethane through extractive distillation process using a particular compound as an extractant (or solvent) from a mixture comprising at least pentafluoroethane (hereinafter, also referred to as "HFC-125") and chloropentafluoroethane (hereinafter, also referred to as "CFC-115"), for example a reaction product from a production process for pentafluoroethane through fluorination of tetrachloroethylene.

BACKGROUND ART

HFC-125 is a useful compound as an alternative chlorofluorocarbon (or flon) compound free of chlorine and is used as a cooling medium, a blowing agent, an injecting propellant and so on. HFC-125 is conventionally produced through a fluorination process of tetrachloroethylene. In such a production process, dichlorotetrafluoroethane, dichlorotrifluoroethane, hexafluoroethane, CFC-115 and so on are produced as by-products.

Among those by-products, CFC-115 has a boiling point of −38.7° C. and HFC-125 which is the desired product has a boiling point of −48.5° C. However, a value of the relative volatility between these two compounds is close to 1. Particularly, when a mixture contains HC-125 at a concentration of not less than 95 mole % (that is, the concentration of CFC-115 is not more than 5 mole %), the relative volatility value is about 1.04. Accordingly, when the above mixture is distilled to separate HFC-125 at a high concentration through a conventional distillation treatment, a distillation apparatus having much plate numbers is required, which generally means that the separation using distillation is extremely difficult.

In the present specification, when a solution comprising at least a remarked component A and a remarked component B (a boiling point of component A<a boiling point of component B) is in a vapor-liquid equilibrium state with the vapor thereof, the term "relative volatility (α)" is defined as follows:

$$\alpha = (Y_A/X_A)/(Y_B/X_B)$$

wherein, $X_A$ is a molar fraction of the lower boiling component A in the liquid phase, $X_B$ is a molar fraction of the higher boiling component B in the liquid phase, $Y_A$ is a molar fraction of the lower boiling component A in the vapor phase which is in equilibrium with its liquid phase, and $Y_B$ is a molar fraction of the higher boiling component B in such vapor phase.

DISCLOSURE OF INVENTION

In order to recover one component from a mixture of a system having a relative volatility value of around 1, an extractive distillation process is adopted. As an example of the extractive distillation process to separate a mixture comprising HFC-125 and CFC-115, U.S. Pat. No. 5,087,329 discloses an extractive distillation process using 1,1,1,2-tetrafluoro-2,2-dichloroethane or 1,1,1-trifluoro-2,2-dichloroethane as an extractant.

In the process disclosed in U.S. Pat. No. 5,087,329, a value of the relative volatility between HFC-125 and CFC-115 is almost 1.2 based on a calculation using figures shown in Example 1 thereof. Thus, when the concentration a 15 of HFC-125 is intended to increase to a ratio of HFC-125/CFC-115=99.7 mole %/0.3 mole % from a mixture having a ratio of HFC-125/CFC-115=7 mole %/93 mole %, a theoretical plate number amounting almost to 40 plates is required in that system according to a theoretical calculation. In this process, a mixture comprising extractant and CFC-115 and HFC-125 is obtained as a bottom product from the extractive distillation step. Thus, it is necessary to sufficiently remove CFC-115 from the bottom product in order to re-use the extractant.

As a result of extensive studies on a process to separate HFC-125 from a mixture comprising HFC-125 and CFC-115 through an extractive distillation process with high efficiency, the present inventors found the matters as follows:

When a mixture comprising at least HFC-125 and CFC-115 is subjected to an extractive distillation process, HFC-125 may be efficiently separated from the above mixture by using, for example, as an extractant (or a solvent), at least one compound (thus, a single compound or a mixture of two or more compounds) selected from the group of hydrofluorocarbon compounds having two carbon atoms.

Accordingly, the present invention provides a process of separating HFC-125 from a mixture comprising at least HFC-125 and CFC-115 through an extractive distillation process, characterized in that compound (thus, a single compound or a mixture of two or more compounds) selected from the group of hydrofluorocarbon compounds having two carbon atoms at least one compound selected from the group of hydrofluorocarbon compounds having two carbon atoms is used as an extractant to obtain HFC-125 in which a concentration of CFC-115 is relatively reduced, and preferably highly concentrated HFC-125 which is free of CFC-115.

That is, the present invention provides a process of producing pentafluoroethane in which a mixture comprising at least pentafluoroethane and chloropentafluoroethane as a main component thereof is subjected to an extractive distillation to obtain another mixture which contains pentafluoroethane as a main component thereof and does not substantially contain chloropentafluoroethane, characterized in that at least one compound selected from the group of hydrofluorocarbon compounds having two carbon atoms is used as an extractant to obtain a mixture comprising pentafluoroethane and the extractant as a main component thereof as a bottom product of the extractive distillation step.

In the present specification, the term "main component" means that the content of the other components is relatively smaller than the content of the main component in the mixture. Concretely, it is sufficient that an amount of the main component is not less than 50%, more concretely not less than 60%, for example not less than 80% (these amount may be on a molar or weight basis). Additionally, in the present specification, the phrase "pentafluoroethane substantially free of chloropentafluoroethane" means that the finally obtainable product is a mixture including pentafluoroethane as its main component, wherein for example, such a mixture may have a concentration of pentafluoroethane not less than 90 weight %, preferably not less than 99.9 weight %, and more preferably not less than 99.99 weight %.

According to the present process when at least one compound selected from the group of hydrofluorocarbon compounds having two carbon atoms is used as an extractant, a mixture may be obtained as a bottom product, which contains pentafluoroethane and the extractant as the main component thereof, preferably a mixture containing chloropentafluoroethane at a concentration not more than 0.1 weight %, and more preferably not more than 0.01 weight %. In this case, the composition and the amount of the distillate product from the extractive distillation is not particularly limited, provided that a ratio of chloropentafluoroethane to pentafluoroethane in the bottom product is reduced by somewhat an extent than an original ratio thereof, preferably the ratio is reduced to not more than 1/10 of the original ratio, and more preferably reduced to not more than 1/100 of the original ratio. In addition, the distillate product may contain, as a main component thereof, chloropentafluoroethane or pentafluoroethane or a mixture of chloropentafluoroethane and pentafluoroethane.

Figure 1:
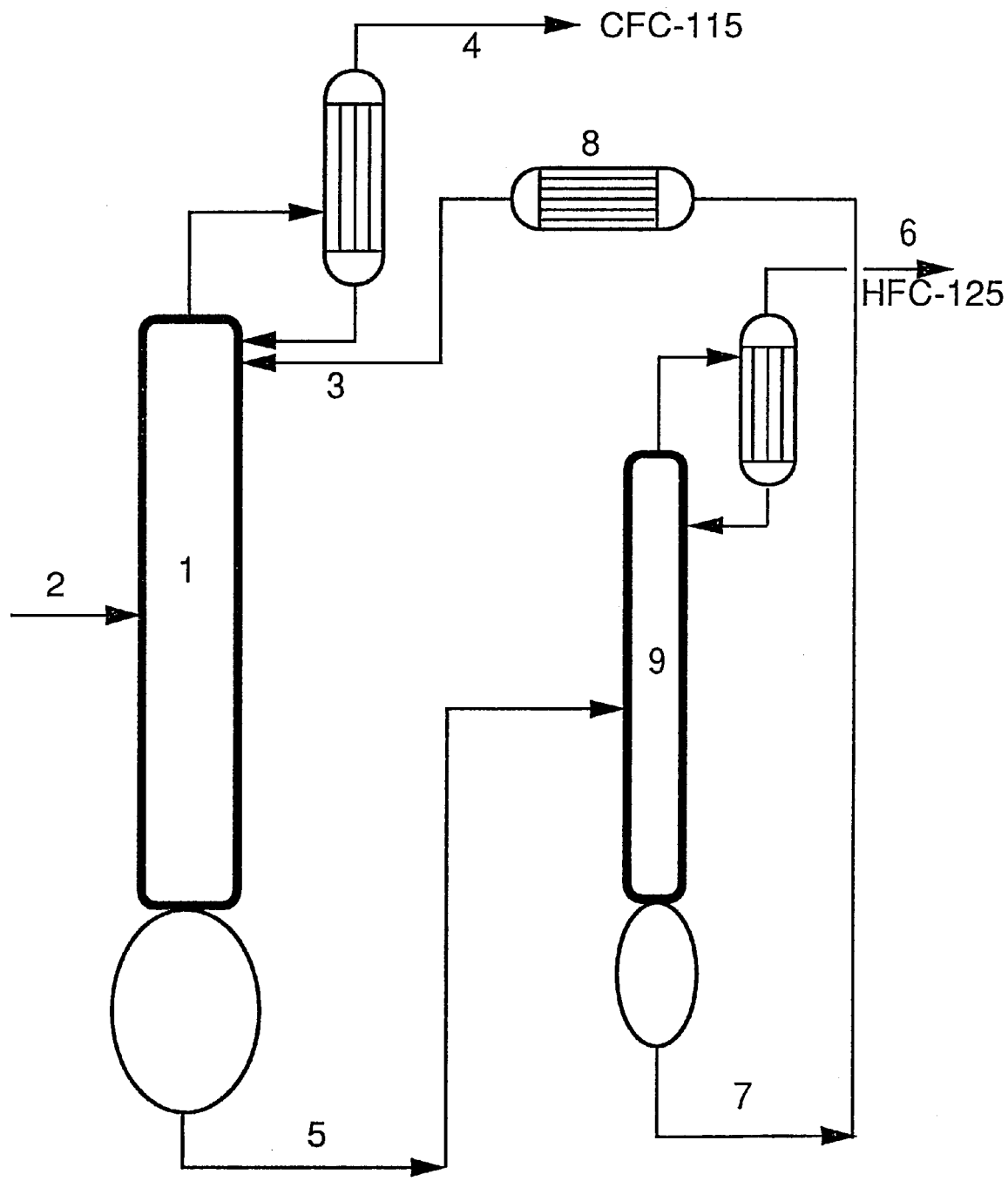
FIG. 1 is a flow sheet schematically showing one concrete embodiment for performing the separating process of the present invention.

In the FIG. 1, the numeral 1 represents an extractive distillation unit, the numeral 2 represents a mixture comprising HFC-125 and CFC-115, the numeral 3 represents an extractant, the numeral 4 represents a distillate, the numeral 5 represents a bottom product, the numeral 6 represents another distillate, the numeral 7 represents another bottom product, and the numeral 8 represents a heat-exchanger, and the numeral 9 represents a separative distillation unit of HFC-125.

BEST MODE FOR CARRYIBNG OUT THE INVENTION

In one embodiment of the present invention, the mixture comprising at least pentafluoroethane and chloropentafluoroethane as its main component substantially consists of two components system consisting of HFC-125 and CFC-115.

In another embodiment of the present invention, pentafluoroethane may be separated from the extractant by subjecting the bottom product from the extractive distillation step, for example a bottom product containing the extractant and pentafluoroethane as its main component, to another distillation treatment, thereby recovering the extractant, which may be recycled to the extractive distillation treatment step. Further, pentafluoroethane may be used for a given purposes.

In the present invention, the term "extractive distillation" means a distillation procedure which is used in the present technical field, in particular in the field of the chemical engineering, characterised in that distillative separation of two components, which are difficult to separate each other through a general distillation procedure, is facilitated by deviating the relative volatility value of the original two-component system from a value of one at a considerable extent by adding a third component.

In the present invention, the hydrofluorocarbon compounds having two carbon atoms are preferably saturated hydrofluorocarbon compounds. Particularly preferred examples of such compounds are 1,1,1,2-tetrafluoroethane ($CF_2CH_2F$ and also referred to HFC-134a), 1,1-difluoroethane ($CF_2HCH_3$ and also referred to HFC-152a), 1,1,1-trifluoroethane ($CF_3CH_3$ and also referred to HFC-143a) and 1,1,2,2-tetrafluoroethane ($CF_2HCF_2H$ and also referred to HFC-134).

The present inventors have studied the extractants as described above which are used in the process of separating HFC-125 from the mixture comprising HFC-125 and CFC-115 by extractive distillation, and obtained measurements of the relative volatilities between HFC-125 and CFC-115 which are shown in Table 1 below:

TABLE 1

| Extractant | Extractant Ratio*) | Relative Volatility ($\alpha$) |
|---|---|---|
| (1) 1,1,1,2-tetrafluoroethane HFC-134a ($CF_3CH_2F$) | 0.25 | 0.907 |
|  | 1.25 | 0.80 |
| (2) 1,1-difluoroethane HFC-152a ($CF_2HCH_3$) | 0.33 | 0.87 |
|  | 0.90 | 0.77 |
| (3) 1,1,1-trifluoroethane HFC-143a ($CF_3CH_3$) | 0.57 | 0.88 |
| (4) 1,1,2,2-tetrafluoroethane HFC-134 ($CF_2HCF_2H$) | 1.20 | 0.80 |

*)Extractant Ratio = (weight of extractant)/(sum of the weights of HFC-125 and CFC-115)
HFC-125/CFC-115 = 98/2 (wt/wt)

When the measurements of Table 1 were obtained, the following manner was employed:

After a sealed vessel was evacuated to an almost vacuum pressure, predetermined amounts of HFC-125, CFC-115 and the extractant, each of them being in liquid phase, were charged into the vessel and were allowed to reach a vapor-liquid equilibrium state at a temperature of 20° C. Then, each composition of the liquid phase and the vapor phase was analyzed using gas chromatography to obtain compositions of the both phases as molar fractions. The relative volatility a was calculated using the above equation:

$$\alpha = (Y_A/X_A)/(Y_B/X_B).$$

Table 1 clearly shows that a relative volatility value alpha ($\alpha$) considerably smaller than one may be obtained when hydrofluorocarbon compounds having 2 carbon atoms which are represented by the compounds (1)–(4) shown in Table 1.

Generally, when a mixture comprising HFC-125 and CFC-115 is subjected to a distillation operation, HFC-125 is concentrated in an overhead fraction (enriched section) of the column since its boiling point is lower than that of CFC-115. On the contrary, when the relative volatility value is smaller than 1, for example, one or more compounds selected from the compounds (1)–(4) are used as the extractant, CFC-115 is concentrated in the top side of the column.

When the extractant is used, which makes the relative volatility value smaller than 1, HFC-125 should be separated from the extractant so as to finally obtain HFC-125 alone since the bottom product from the extractive distillation step contains the extractant as described above. This separation is easily carried out with a conventional distillation operation using a plate column or a packed column since a boiling point difference is large between HFC-125 and the extractant, for example, the boiling point difference is 22°C. when HFC-134a is used as the extractant. Thus, HFC-125 may be effectively separated from the mixture comprising at least HFC-125 and CFC-115 by using combination of the extractive distillation operation with the distillation operation thereafter which separates the extractant.

If the mixture to be separated contains a third component in addition to HFC-125 and CFC-115, only difference resides in that the third component behaves together with HFC-125 and/or CFC-115 depending on a boiling point of the third component. Thus, even if the third component is contained in the mixture, HFC-125 is separated from CFC-115 by carrying out the extractive distillation using the extractant according to the present invention.

Further, with respect to the re-use of the extractant in the extractive distillation step, when the extractant disclosed in U.S. Pat. No. 5,087,329 which is referred to in the above is used, CFC-115 is concentrated in the bottom fraction (recovery section) and the extractant is also recovered at the bottom fraction, which means that a bottom product containing a large amount of the extractant and CFC-115 is obtained. Thus, it is necessary to separate CFC-115 from the extractant sufficiently when the extractant is intended to be re-used. When a small amount of CFC-115 might remain in the extractant, it may fall out that CFC-115 is added to the extractive distillation step, whereby extraction efficiency may deteriorate and the required number of the theoretical plate may increase. In fact, it is estimated that the required number of the theoretical plate of a distillation apparatus would become a considerably large number in order to separate CFC-115 without deteriorating the extraction efficiency.

On the other hand, in the process according to the present invention wherein the extractant making the relative volatility smaller than one such as the extractant selected from the compounds (1)–(4) mentioned above is used, for example, the bottom product from the extractive distillation step is substantially free of CFC-115 so that it is sufficient to separate only HFC-125 from the extractant. Therefore, even though HFC-125 remains in the extractant at a concentration of a few percentages and such extractant is re-used in the extractive distillation step, almost no effect is observed on the extraction efficiency. Thus, the number of theoretical plate of the distillation apparatus required for the recovery of the extractant may be merely around 10. Hence the present process has the advantage over the process disclosed in the U.S. Patent referred to in the above.

The extractive distillation process using the extractant according to the present invention can be carried out any distillation apparatus which is conventionally used such as a plate column, a packed column and so on. There are no specific limitations on various conditions of the distillation apparatus (such as an operation temperature, an operation pressure, a reflux ratio, a total plate number of the distillation apparatus, plate levels of mixture being fed and extractant being fed and so on), and proper conditions may be selected depending on aimed separation. Since HFC-125 and CFC-115 have considerably low boiling points, it is generally preferable to carry out the extractive distillation under a pressurized condition. The operation pressure may be for example in the range between 0 and 30 Kg/cm$^2$-G (gauge pressure), and preferably in the range between 10 and 15Kg/cm$^2$-G. In order to carry out the distillation operation economically considering operation temperatures of a condenser and a reboiler, the temperature at the top of the distillation apparatus is preferably in the range from −10 to 35° C. and the temperature at the bottom of the distillation apparatus is preferably in the range from 20 to 60° C.

The process of the present invention may be carried out in a batch mode or a continuous mode. Although in some cases, the process may be carried out in a semi-continuous mode wherein withdrawal and/or feed is carried out intermittently, the extractant should be continuously supplied to the distillation apparatus.

In the process of the present invention, a ratio (S/F) of an amount (S) of the extractant to an amount (F) of the feed mixture (namely, HFC-125 and CFC-115) has an effect on an extent of the separation. Generally, the ratio may be properly selected depending on a composition of HFC-125/CFC-115 of the mixture to be subjected to the extractive distillation, an allowable concentration of CFC-115 which remains in the separated HFC-125 and so on. A required number of theoretical plate of the extractive distillation apparatus may be properly selected in combination with the selection of the ratio (S/F).

In general, preferable separation may be achieved with the ratio based on weight in the range from about 0.1 to about 10, and preferably in the range from about 0.5 to about 5. For example, in order to achieve a separation wherein a mixture of CFC-115 (1mol %) and HFC-125 (99 mol %) is subjected to the extractive distillation using the extractant selected from the compounds (1)–(4), whereby CFC-115 is distilled as a fraction having a concentration of 10 mol % (thus, 90mol % of HFC-125 concentration) and also an HFC-125 stream is finally obtained of which CFC-115 concentration is not more than 0.1 mol % (thus, more than 99.9 mol % of HFC-125 concentration) after the separation from the extractant, it is sufficient that the required number of theoretical plate in the extractive distillation is in the range of for example about 5 to 10 and the weight ratio of the extractant to the mixture consisting of HFC-125 and CFC-115 is in the range of for example about 2 to 4.

The present invention will be explained in detail with reference to the flow-sheet in FIG. 1 as an example wherein the extractant compound which makes the relative volatility value between HFC-125 and CFC-115 smaller than 1 is used and wherein HFC-134a is used as the extractant including the re-use thereof.

A mixture 2 comprising HFC-125 and CFC-115 (for example HFC-125/CFC-115=98 mol %/2mol %) is supplied to an extractive distillation apparatus 1 which is operated under a pressurized condition (for example 13 Kg/cm$^2$-G). For example, an apparatus having the number of theoretical plate of about twenty is used as the distillation apparatus 1. Extractant 3 is supplied to the distillation apparatus 1 (for example, onto the 5th theoretical plate from the top) in an amount of about twice by weight as much as that of the mixture 2. Under those conditions, for example, when the mixture is supplied onto the tenth theoretical plate from the top and a reflux ratio is set for five hundred, a mixture of HFC-125/CFC-115 (for example 80 mol %/20 mol %) may be withdrawn from the top as a distillate product 4.

In addition, a mixture of HFC-125/CFC-115(for example 99.9 mol %/0.1 mol %), which further contains HFC-134a, may be withdrawn from the bottom as a bottom product 5 (HFC-134a concentration is 70% by weight). Then, the bottom product may be supplied to a distillation apparatus 9 (theoretical plate: 10) onto the 10th theoretical plate from the top, which is operated under a pressurized condition (for example (13 Kg/cm$^2$-G), and HFC-125 substantially free of CFC-115 and HFC-134a may be obtained as a distillate product 6 from the top (the reflux ratio: 10). HFC-134a which is substantially free of HFC-125 is recovered from the bottom of the distillation apparatus 9 (theoretical plate: 10) as a bottom product 7, which is then supplied to the extractive distillation apparatus 1 to be re-used as the extractant. HFC-134a to be re-used may be optionally heated or cooled as required through a heat exchanger 8 before being supplied to the distillation apparatus 1.

In the process of the present invention, the level of the plate onto which the extractant is supplied is preferably above a plate onto which the mixture is supplied when the boiling point of the extractant is higher than that of the mixture. Thus, the plate onto which a reflux is returned and the plate onto which the extractant is supplied may be the same. On the contrary, the level of the plate onto which the extractant is supplied is preferably positioned below the plate onto which the mixture is supplied. Optionally, the plate onto which the mixture is supplied and the plate onto which the extractant is supplied may be the same. Alternatively, before the mixture is fed to the distillation apparatus, it may be mixed with the extractant and then the resulted mixture may be supplied to the distillation apparatus.

Concretely, when HFC-134a is used as the extractant, it is more preferable to supply HFC-134a onto a plate which is positioned about 5 to 10 theoretical plates above the plate onto which the mixture is supplied.

Employing the apparatus and the operation conditions as described above, HFC-125 which is free of CFC-115 can be separated from the mixture comprising HFC-125 and CFC-115.

EXAMPLES

Example 1

Into an Alder-Shaw type fractionating column having a diameter of 20 mm (theoretical plate number: 13), a mixture of 40 g (0.39 mol) of HFC-134a and 82 g (0.68 mol) of HFC-125 which contains 2 mol % of CFC-115 (thus, the percentage of HFC-125 is 98 mol %) is supplied, while the top of the column being cooled with dry ice/acetone and refluxed under a normal pressure. After holding a total reflux condition for about an hour, the overhead fraction had a composition of CFC-115/HFC-125=4.6/95.4 (mol/mol) and the still fraction had a composition of CFC-115/HFC-125= 1/99 (mol/mol) (CFC-115/HFC-125/HFC-134a=0.62/66/32.7). Accordingly, the concentration of CFC-115 in the still fraction could be reduced to a value of 1% as opposed to the value of 2% in the feed composition.

EXAMPLE 2

Using an extractive distillation column equipped with a condenser at its top, a mixture of HFC-125 and CFC-115 (HFC-125/CFC-115=99/1 (wt/wt)) was treated. The distillation column had a diameter of 100 mm and 25 theoretical plates (actual plate number was 50), and it was operated under a pressure of about 11 Kg/cm$^2$-G. HFC-134a as the extractant was supplied onto the 5th theoretical plate from the top, and the mixture to be distilled was supplied at a temperature of 25° C. onto the 10th theoretical plate from the top.

Concentrated CFC-115 (containing HFC-125) was withdrawn as a distillate product from the top. This operation was carried out at a reflux ratio of 200. A mixture of HFC-125 and HFC-134a was withdrawn from the bottom at a temperature of 30° C., CFC-115 content in which was reduced to 0.1 % by weight.

Mass balance of the above operation is shown in Table 2 below:

TABLE 2

|  | total flow rate (Kg/hr) | HFC-125 (wt %) | CFC-115 (wt %) | HFC-134a (wt %) |
| --- | --- | --- | --- | --- |
| (input) |  |  |  |  |
| Extractant (HFC-134a) | 50 |  |  | 100 |
| HFC-125/CFC-115 | 10 | 99 | 1 |  |

TABLE 2-continued

|  | total flow rate (Kg/hr) | HFC-125 (wt %) | CFC-115 (wt %) | HFC-134a (wt %) |
| --- | --- | --- | --- | --- |
| mixture (output) |  |  |  |  |
| Distillate product | 1 | 90.9 | 9.0 | 0.1 |
| Bottom product | 59 | 16.4 | 0.015 | 83.6 |

The bottom product withdrawn from the bottom of the distillation apparatus, which contained HFC-125, HFC-134a and small amount of CFC-115 was supplied to another distillation apparatus having a diameter of 80 mm and 50 theoretical plates (the number of actual plate was 70) which was operated under an operation pressure of 13 Kg/cm$^2$-G and a reflux ratio of 10, whereby a distillate product having a ratio of HFC-125 (99.9 weight %)/CFC-115 (0.1 weight %) was obtained from the top and HFC-134a stream containing 2% by weight of HFC-125 was obtained from the bottom as a bottom product. The content of CFC-115 in the bottom product was less than 0.01% by weight. Thus obtained HFC-134a stream can be re-used as the extractant for the extractive distillation.

What is claimed is:

1. A process of producing pentafluoroethane by subjecting a mixture comprising at least pentafluoroethane and chloropentafluoroethane to an extractive distillation process so as to obtain pentafluoroethane which is substantially free of chloropentafluoroethane, which process comprises the steps of:

supplying the mixture to the extractive distillation process, supplying at least one compound selected from the group consisting of 1,1,1,2-tetrafluroethane, 1,1-difluoroethane, 1,1,1, trifluoroethane and 1,1,2,2,-tetrafluoroethane, which compound makes a relative volatility value between pentafluoroethane and chloropentafluoroethane smaller than 1as an extractant to the extractive distillation process, and obtaining a mixture comprising pentafluoroethane and the extractant as the main component thereof as a bottom product from the extractive distillation process.

2. The process according to claim 1 wherein the mixture and the extractant are mixed together, which is then supplied to the extractive distillation process.

3. The process according to claim 1 or 2 wherein a weight ratio (S/F) of the extractant (S) used in the extractive distillation process to pentafluoroethane and chloropentafluoroethane (F) which are contained in the mixture to be supplied to the extractive distillation process is in the range from 0.1to 10.

4. The process according to claim 1 wherein pentafluoroethane is separated by distilling the mixture comprising pentafluoroethane and the extractant as the main component thereof obtained as a bottom product from the extractive distillation process, whereby a mixture containing the extractant as the main component thereof is recovered and re-used in the extractive distillation process.

\* \* \* \* \*